(12) United States Patent
Chiba et al.

(10) Patent No.: US 7,087,037 B2
(45) Date of Patent: Aug. 8, 2006

(54) SYRINGE

(75) Inventors: Atsushi Chiba, Tokyo (JP); Kazuhiro Ichikawa, Tokyo (JP)

(73) Assignee: Kabushiki Kaisha Top, Tokyo (JP)

( * ) Notice: Subject to any disclaimer, the term of this patent is extended or adjusted under 35 U.S.C. 154(b) by 281 days.

(21) Appl. No.: 10/203,878

(22) PCT Filed: Mar. 9, 2001

(86) PCT No.: PCT/JP01/01869

§ 371 (c)(1),
(2), (4) Date: Aug. 15, 2002

(87) PCT Pub. No.: WO01/70310

PCT Pub. Date: Sep. 27, 2001

(65) Prior Publication Data

US 2003/0014005 A1 Jan. 16, 2003

(30) Foreign Application Priority Data

Mar. 17, 2000 (JP) ........................... 2000-075668

(51) Int. Cl.
*A61M 5/178* (2006.01)

(52) U.S. Cl. ........................................... 604/38
(58) Field of Classification Search ............. 604/18–19, 604/27, 68, 82, 181, 182, 186, 187, 191, 604/207, 218, 221, 222, 228, 264, 272, 290; 128/919

See application file for complete search history.

(56) References Cited

U.S. PATENT DOCUMENTS 5,496,285 A * 3/1996 Schumacher et al. ....... 604/218

FOREIGN PATENT DOCUMENTS

| EP | 0 689 847 A1 | 1/1996 |
| EP | 0689847 A1 * | 1/1996 |
| FR | 1 346 470 A | 12/1963 |
| GB | 1 106 825 A | 3/1968 |
| JP | 58-69574 A | 4/1983 |
| JP | 7-513 A | 1/1995 |

* cited by examiner

*Primary Examiner*—Nicholas D. Lucchesi
*Assistant Examiner*—Michael M Thompson
(74) *Attorney, Agent, or Firm*—Birch, Stewart, Kolasch & Birch, LLP

(57) ABSTRACT

There is provided an injector having a gasket held in excellent intimate contact with an inner wall surface of a barrel and shortened in overall length. A gasket is joined to a mount base disposed on a tip end of a plunger and having a bendable portion which bends toward an axis of the plunger radially outwardly of the mount base. The gasket is joined to the mount base with a gap left for allowing the bendable portion to bend toward the tip end of the plunger when the gasket slides toward an injection needle. The gasket is made of a synthetic resin having an A-scale Shore hardness in the range from 20 to 70. The gasket has a groove define therein radially outwardly of the mount base, and the bendable portion comprises a portion of the gasket disposed radially outwardly of the groove.

3 Claims, 5 Drawing Sheets

SYRINGE

BACKGROUND OF THE INVENTION

This application is the national phase under 35 U.S.C. § 371 of PCT International Application No. PCT/JP01/01869 which has an International filing date of Mar. 9, 2001, which designated the United States of America.

1. Field of the Invention

The present invention relates to an injector made of synthetic resin.

2. Description of Related Art

There has heretofore been known an injector 31 of synthetic resin, as shown in FIG. 6 of the accompanying drawings, as a disposable injector, for example. The injector 31 comprises a barrel 4 of synthetic resin having a luer taper fitting 3 for mounting an injection needle 2 thereon, and a plunger 5 of synthetic resin having on its tip end a gasket 32 held in intimate sliding contact with an inner wall surface 4a of the barrel 4. The plunger 5 is made of polypropylene, polystyrene, polycarbonate, or the like, and has a crown-shaped projection 34 on its tip end which has a radially projecting flange 33.

The gasket 32 is complementary in shape to the crown-shaped projection 34, and is snugly fitted over the crown-shaped projection 34. The gasket 32 includes a sliding ridge 35 positioned radially outwardly of and aligned with the crown-shaped projection 34, and is made of an elastic synthetic resin so that the gasket 34 can be held in intimate sliding contact with the inner wall surface 4a of the barrel 4. When a medicine is drawn into the barrel 4, the plunger 5 is pulled to develop a negative pressure in the barrel 4. At this time, since the gasket 32 is securely locked on the flange 33, the gasket 32 is prevented from being detached from the crown-shaped projection 34 under the negative pressure.

The conventional injector 31 shown in FIG. 6 is disadvantageous in that the overall length of the injector 31 is large because of the projection 34 that is constructed to prevent the gasket 32 from being dislodged out of position. The gasket 32 fitted over the projection 34 is made of a material which is different from the material of the projection 34. Therefore, the gasket 32 and the projection 34 need to be prepared separately and then combined together subsequently.

BRIEF SUMMARY OF THE INVENTION

It is therefore an object of the present invention to provide an injector which is shortened in overall length and can easily be manufactured.

Another object of the present invention is to provide an injector which has a gasket held in excellent intimate contact with an inner wall surface of a barrel.

To achieve the above objects, there may be proposed an injector having a gasket joined, as by thermal fusion or the like, to a tip end of a plunger made of a thermoplastic synthetic resin, the gasket being made of a synthetic resin, such as a thermoplastic elastomer, which can be held in excellent intimate contact with an inner wall surface of a barrel. However, when one region of the synthetic resin remains to be kept in intimate contact with the inner wall surface of the barrel over a long period of time during storage or the like, the region suffers creep, and its intimate contact with the inner wall surface of the barrel is reduced.

According to the present invention, there is provided an injector comprising a barrel for mounting an injection needle thereon and a plunger with a gasket joined to a tip end thereof and held in intimate sliding contact with an inner wall surface of the barrel, the gasket being joined to a mount base mounted on the tip end of the plunger and smaller in diameter than the tip end of the plunger, the gasket being joined to a mount base disposed on a tip end of the plunger and smaller in diameter than the tip end of the plunger, the gasket having a bendable portion which bends toward an axis of the plunger radially outwardly of the mount base when the gasket is held in intimate contact with an inner wall surface of the barrel and slides toward a tip end of the barrel, the gasket being joined to the mount base with a gap left for allowing the bendable portion to bend toward the tip end of the plunger.

With the injector according to the present invention, since the gasket may be joined to the tip end of the plunger, but does not need to be held in engagement with the tip end of the plunger, the injector can be shortened in overall length.

With the injector according to the present invention, the gasket is held at its bendable portion in intimate contact with the inner wall surface of the barrel. When the plunger is moved along the inner wall surface of the barrel, the bendable portion bends toward the axis of the plunger. Specifically, when the plunger slides toward the rear end of the barrel in order to draw a medicine, a negative pressure is developed in the injector, the bendable portion bends away from the plunger. When the plunger slides toward the tip end of the barrel in order to inject a medicine into a patient, the bendable portion is pressed and bends toward the plunger.

The gasket is joined to the mount base disposed on the tip end of the plunger and smaller in diameter than the tip end of the plunger, with a gap left for allowing the bendable portion to bend toward the tip end of the plunger. Therefore, the bendable portion can bend into a space defined radially outwardly of the mount base toward the tip end of the plunger.

As a result, the gasket is held at its portion different from a usual portion in intimate contact with the inner wall surface of the barrel. Even if the gasket suffers creep during storage, it is held in excellent intimate contact with the inner wall surface of the barrel without being affected by the creep.

In order to keep the bendable portion in intimate contact with the inner wall surface of the barrel and allow the bendable portion to respond sharply to the negative pressure developed when the medicine is drawn or the positive pressure developed when the medicine is injected, the gasket should preferably made of a synthetic resin having an A-scale Shore hardness in the range from 20 to 70. If the A-scale Shore hardness were less than 20, then the gasket would be liable to suffer creep and might not be held in sufficient intimate contact with the inner wall surface of the barrel. If the A-scale Shore hardness were in excess of 70, the flexibility of the bendable portion would be so reduced that it would be difficult for the bendable portion to bend in response to the negative pressure developed when the medicine is drawn or being pressed when the medicine is injected.

In the injector according to the present invention, the gasket has an annular groove defined in a surface thereof remote from the plunger and disposed radially outwardly of the mount base, the bendable portion comprising a portion of the gasket disposed radially outwardly of the annular groove, whereby the bendable portion can bend about a bottom of the annular groove. With this structure, the gasket allows the bendable portion to bend easily.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and of the scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Embodiments of the present invention will hereinafter be described in detail with reference to the drawings.

Figure 1:
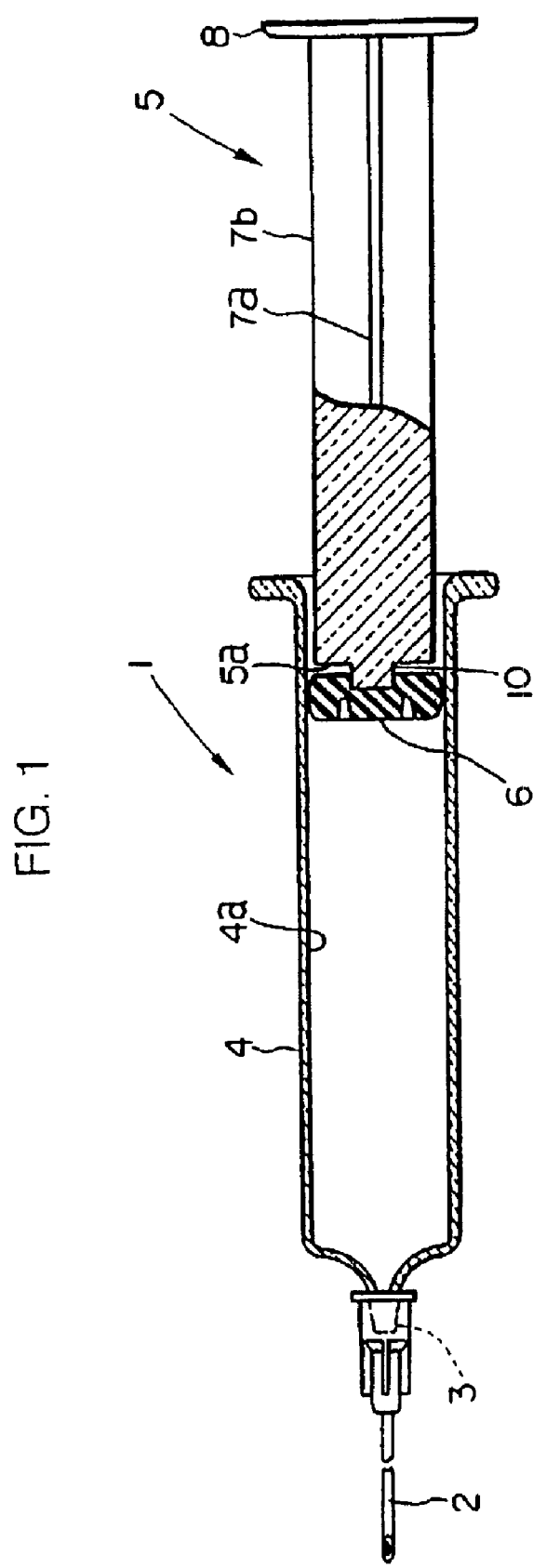
FIG. 1 is a cross-sectional view of an injector according to an embodiment of the present invention.

As shown in FIG. 1, an injector 1 according to an embodiment of the present invention comprises a barrel 4 of synthetic resin having a luer taper fitting 3 for mounting an injection needle 2 thereon, and a plunger 5 of synthetic resin having on its tip end 5a a gasket 6 held in intimate sliding contact with an inner wall surface 4a of the barrel 4.

The plunger 5 is made of a synthetic resin such as polystyrene, polyolefin, polyester, polyamide, polyvinyl chloride, polycarbonate, acrylonitrile-butadiene-styrene copolymer, or the like, for example. The plunger 5 comprises a pair of plates 7a, 7b combined in a crisscross pattern, and has a disk 8 on its rear end that serves as a thumb rest and a disk-shaped flange 9 (see FIGS. 3(a) and 3(b)) on its front end. The flange 9 has a mount base 10 to which the gasket 6 is joined.

Figure 2:
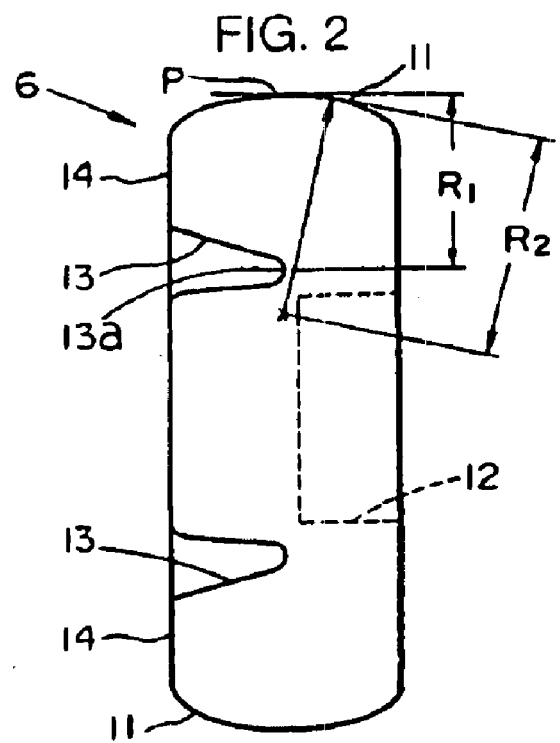
FIG. 2 is an enlarged cross-sectional view of a gasket of the injector shown in FIG. 1.

As shown at an enlarged scale in FIG. 2, the gasket 6 is substantially in the form of a disk having a laterally outwardly projecting curved side surface 11 held in intimate contact with the inner wall surface 4a of the barrel 4. The gasket 6 has a hole 12 defined in its surface towards the plunger 5 to be fitter with the mount base 10, and an annular groove 13 defined in its surface remote from the plunger 5 and having a diameter greater than the diameter of the mount base 10. The gasket 6 has a bendable portion 14 positioned radially outwardly of the annular groove 13.

The bendable portion 14 can bend toward the axis of the plunger 5 about the bottom 13a of the annular groove 13 when the gasket 6 slides along the inner wall surface 4a of the barrel 4. The bendable portion 14 is constructed such that the distance $R_1$ between the bottom 13a of the annular groove 13 and the crest P of the curved side surface 11 is smaller than the radius $R_2$ of curvature of the curved side surface 11.

Operation of the gasket 6 will be described below with reference to FIGS. 3(a) and 3(b).

Figure 3A:
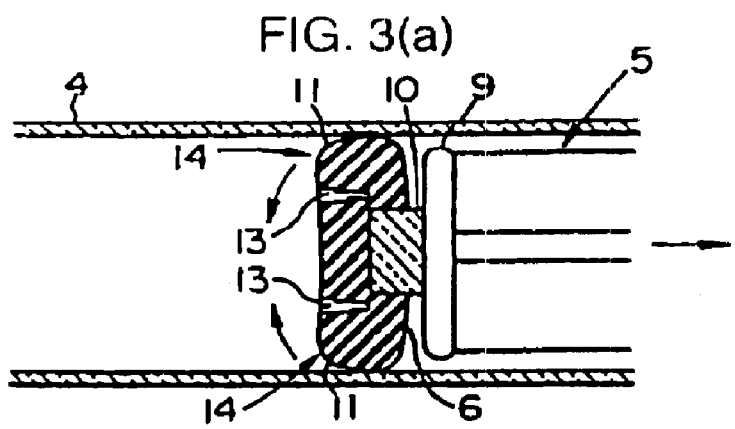
FIGS. 3(a) and 3(b) are cross-sectional views illustrative of the manner in which the injector shown in FIG. 1 operates.

When plunger 5 is pulled to draw a medicine into the barrel 4 in the direction indicated by the arrow in FIG. 3(a), a negative pressure is developed in the barrel 4. The bendable portion 14 bends into the annular groove 13 under the developed negative pressure. As a result, a portion of the curved side surface 11 that is closer to the plunger 5 than the crest P is held in intimate contact with the inner wall surface 4a of the barrel 4.

Figure 3B:
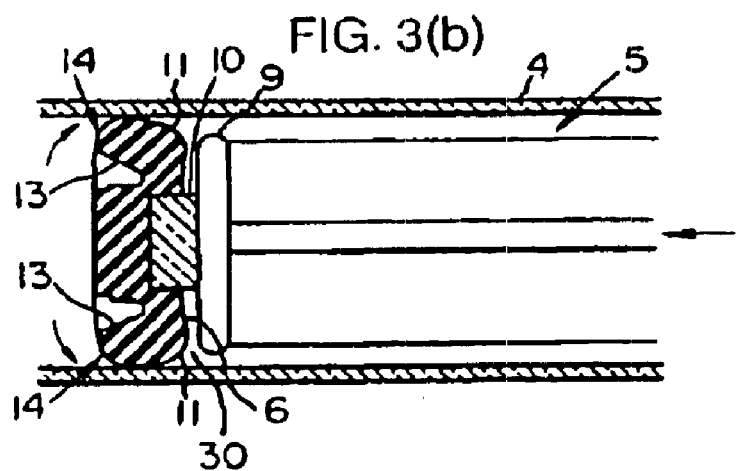

When the plunger 5 is pushed to inject the medicine from the barrel 4 into a patient in the direction indicated by the arrow in FIG. 3(b), since a positive pressure is applied to the gasket 6, the bendable portion 14 bends toward the plunger 5. At this time, because the mount base 10 is smaller in diameter than the flange 9 and the gasket 6 is joined to the mount base 10 in spaced relation to the flange 9, the bendable portion 14 can bend into a gap 30 defined radially outwardly of the mount base 10. As a result, a portion of the curved side surface 11 that is remoter from the plunger 5 than the crest P is held in intimate contact with the inner wall surface 4a of the barrel 4.

The crest P of the curved side surface 11 is usually held in intimate contact with the inner wall surface 4a of the barrel 4. However, when the gasket 6 slides along the inner wall surface 4a of the barrel 4, a portion of the curved side surface 11 other than the crest P is held in intimate sliding contact with the inner wall surface 4a of the barrel 4. Therefore, even if the gasket 6 is suffering creep, the gasket 6 is held in excellent intimate contact with the inner wall surface 4a of the barrel 4 regardless of the creep.

The gasket 6 is molded of a synthetic resin whose spring-loaded indenter hardness (A-scale Shore hardness) measured by an A-scale durometer as specified by JIS K6301 ranges from 20 to 70 in order to allow the bendable portion 14 to bend easily and also to be held in intimate contact with the inner wall surface 4a of the barrel 4.

The A-scale Shore hardness can be selected in the above range depending on the capacity of the injector 1. For example, if the injector 1 is of a small diameter and has a nominal capacity ranging from 1 to 3 milliliters, then it may be molded of a soft synthetic resin, and if the injector 1 is of a large diameter and has a nominal capacity ranging from 30 to 100 milliliters, then it may be molded of a hard synthetic resin.

Synthetic resins whose A-scale Shore hardness is in the above range include a thermoplastic elastomer such as a polystyrene elastomer, a polyolefin elastomer, a polyester elastomer, a polyamide elastomer, a polyvinyl chloride elastomer, or the like, or styrene-butadiene rubber (SBR) with polystyrene added, or the like.

The polystyrene elastomer may be styrene-butadiene-styrene block copolymer, styrene-isoprene-styrene block copolymer, styrene-ethylene-butylene-styrene block copolymer, styrene-ethylene-propylene-styrene block copolymer, or the like.

The polyolefin elastomer may be a combination of a hard segment such as polypropylene (PP), polyethylene (PE), polystyrene (PS), acryronitrile-butadiene-styrene copolymer (ABS), acrylonitrile-styrene copolymer (AS), polymethyl methacrylate (PMMA), polytetramethylene terephthalate (PTMT), polyamide (PA), polycarbonate (PC), or the like, and a soft segment such as isobutylene-isoprene rubber (IIR), etylene-propylene-diene terpolymer, polytranspentenamer (PTPR), natural rubber (NR), butadiene rubber (BR), chloroprene rubber (CR), styrene-butadiene rubber (SBR), ethylene-vinyl acetate copolymer (EVA), alkylester acrylate-2-chloroethylvinylether copolymer (ACM), chlorinated polyethylene (CPE), nitrile-butadiene rubber (NBR), or the like.

The polyester elastomer may be polyester-polyether multiblock copolymer, polyester-polyester multiblock copolymer, or the like. The polyamide elastomer may be polyamide-polyether multiblock copolymer, polyamide-polyester multiblock copolymer, or the like.

The polyvinyl chloride elastomer may be a blended combination of polymeric polyvinyl chloride and plasticized polyvinyl chloride, a blended combination of partially crosslinked polyvinyl chloride and plasticized polyvinyl chloride, polyvinyl chloride-elastomer alloy, or the like.

The polyvinyl chloride-elastomer alloy may includes, as a soft segment, partially crosslinked nitrile-butadiene rubber, a polyurethane elastomer, a polyester elastomer, or the like.

In the above embodiment, the gasket 6 has the annular groove 13 defined in its surface remote from the plunger 5 and positioned radially outwardly of the mount base 10, and the bendable portion 14 positioned radially outwardly of the annular groove 13. However, the gasket 6 may be of any shape insofar as it has the bendable portion 14 that is positioned radially outwardly of the mount base 10 and operates as shown in FIGS. 3(a) and 3(b) when the plunger 5 is pulled and pushed.

Figure 4A:
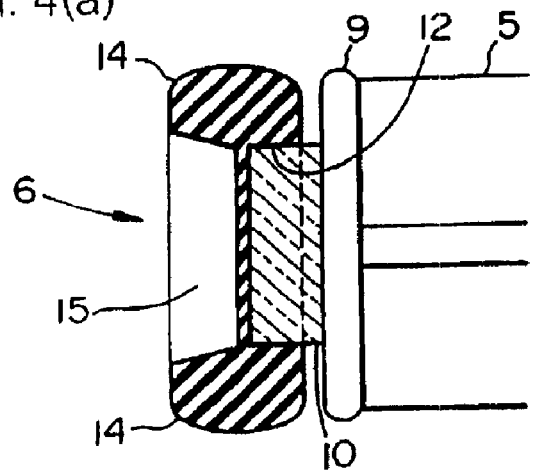
FIGS. 4(a) through 4(c) are cross-sectional views of injectors according to other embodiments of the present invention.
Figure 4B:
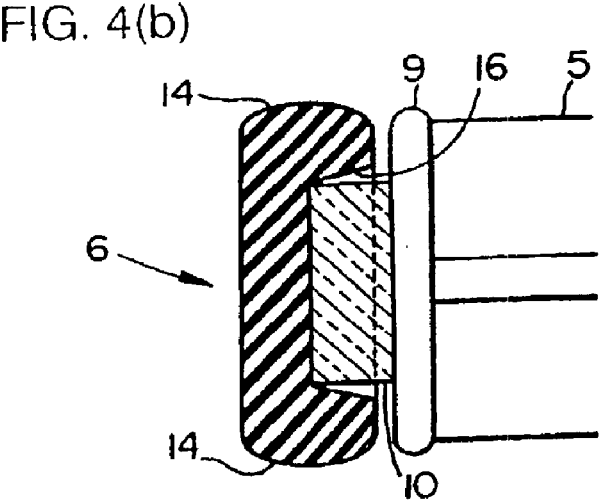
Figure 4C:
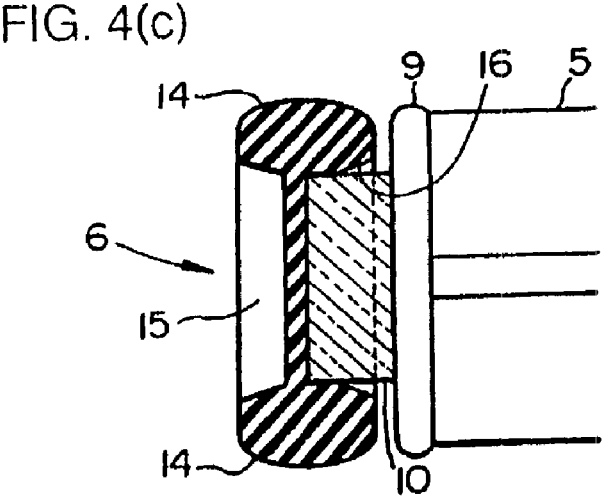

FIGS. 4(a) through 4(c) show gaskets 6 of different shapes by way of example.

FIG. 4(a) shows a gasket 6 having a recess 15 defined in its surface remote from the plunger 5 and having a diameter greater than the diameter of the mount base 10. The gasket 6 has a bendable portion 14 disposed radially outwardly of the recess 15.

FIG. 4(b) shows a gasket 6 having a recess 16 defined in its surface close to the plunger 5 and having a diameter greater than the diameter of the mount base 10. The mount base 10 is joined to the recess 16. The gasket 6 has a bendable portion 14 disposed radially outwardly of the recess 16.

FIG. 4(c) shows a gasket 6 having a recess 15 defined in its surface remote from the plunger 5 and having a diameter greater than the diameter of the mount base 10, and a recess 16 defined in its surface close to the plunger 5 and having a diameter greater than the diameter of the mount base 10. The mount base 10 is disposed in and joined to the recess 16. The gasket 6 has a bendable portion 14 disposed radially outwardly of the recesses 15, 16.

The gasket 6 may be joined to the mount base 10 of the plunger 5 by a thermal fusion process. In the thermal fusion process, the gasket 6 and the mount base 10 are pressed together while being heated. According to the thermal fusion process, the gasket 6 is molded of a synthetic resin that can thermally be fused to the material of the plunger 5, selected from the above synthetic resins indicated as materials of the gasket 6.

The thermal fusion process for pressing the gasket 6 and the mount base 10 while they are being heated will be described below.

Figure 5:
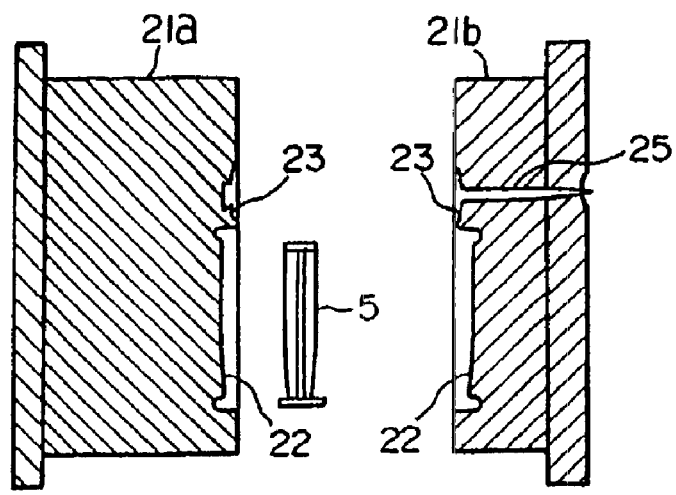
FIGS. 5(a) through 5(c) are cross-sectional views showing a method of manufacturing an injector according to the present invention.

First, the plunger 5 of polypropylene, for example, is manufactured according to a known injection molding process. Then, as shown in FIG. 5(a), the plunger 5 is set in a mold assembly of molds 21a, 21b. The molds 21a, 21b jointly have a cavity 22 complementary in shape to the plunger 5 and the gasket 6, and a pin-point gate 23 positioned at the center of a surface of the gasket 6 to be molded. The mold 21b has a runner 25 for interconnecting the pin-point gate 23 and an injection molding machine 24 (see FIG. 5(c)).

Figure 5B:
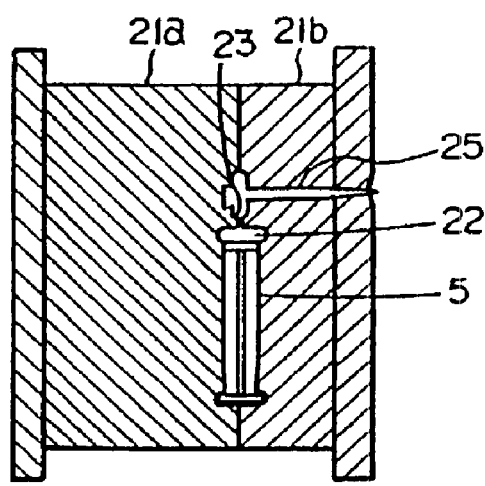
Figure 5C:
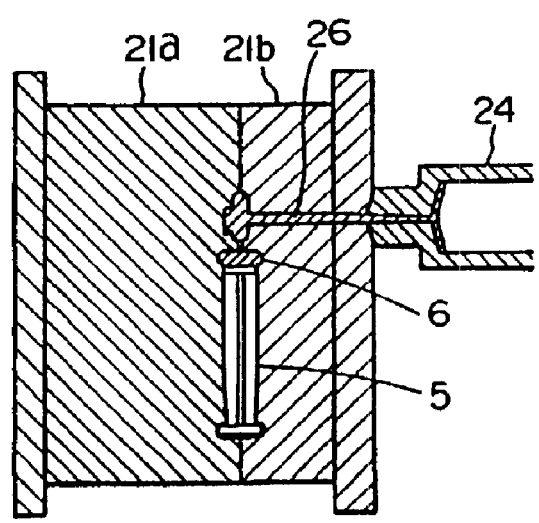
Figure 6:
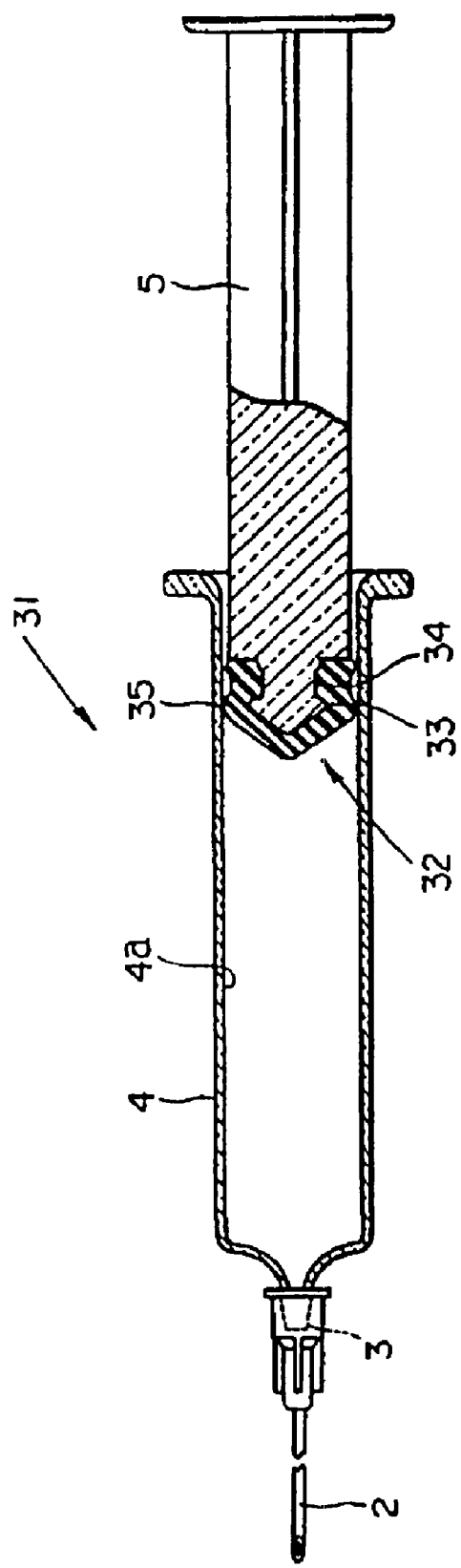
FIG. 6 is a cross-sectional view of a conventional injector.

As shown in FIG. 5(b), the molds 21a, 21b with the plunger 5 set therein are closed. Then, as shown in FIG. 5(c), the injection molding machine 24 is connected to the runner 25 in the mold 21b, and injects a styrene elastomer 26, for example, in a molten state into the cavity 22. The gasket 6 is now thermally fused to the plunger 5 with the heat and pressure produced when the styrene elastomer 26 is injected, so that the plunger 5 and the gasket 6 can integrally be joined together.

In the thermal fusion process, the pre-molded plunger 5 is set in the molds 21a, 21b. However, the gasket 6 may be pre-molded, and then set on the molds 21a, 21b.

The gasket 6 may be joined to the mount base 10 of the plunger 5 by a solvent welding process or an adhesive bonding process. In the solvent welding process, the gasket 6 and the plunger 5 are partly dissolved by a solvent common, and then joined to each other. In the adhesive bonding process, the gasket 6 and the plunger 5 are bonded to each other with an adhesive. If the gasket 6 are to be joined to the mount base 10 of the plunger 5 by the solvent welding process or the adhesive bonding process, then the gasket 6 may be molded of any synthetic resins insofar as they exhibit adhesiveness to the material of the plunger 5 with an adhesive, an organic solvent, or the like.

INDUSTRIAL APPLICABILITY

The present invention can be utilized to manufacture disposable injectors for use as a medical instrument.

The invention being thus described, it will be obvious that the same may be varied in many ways. Such variations are not to be regarded as a departure from the spirit and scope for the invention, and all such modifications as would be obvious to one skilled in the art are intended to be included within the scope of the following claims.

What is claimed is:

1. An injector comprising a barrel for mounting an injection needle thereon and a plunger with a gasket joined to a tip end thereof and held in intimate sliding contact with an inner wall surface of the barrel, said gasket being of substantial plate-shape, an entire side surface thereof being a curved surface having a convex-shaped are rising in the direction of the inner wall surface of the barrel and extending along an axis direction of the plunger, and being held in intimate contact with the inner wall surface of the barrel at a portion of the curved surface thereof, said gasket being joined to a mount base, the mount base being disposed on a tip end of the plunger and being smaller in diameter than the tip end of the plunger, with a gap being left, the gap allowing said gasket to be bendable toward the tip end of the plunger, said gasket having an annular groove defined in a surface thereof remote from said plunger and larger in diameter than said mount base, said gasket having a bendable portion, which bends about a bottom of said annular groove in such a manner that the bendable portion falls in a direction radially outwardly with respect to said gasket when the gasket is held in intimate contact with an inner wall surface of the barrel and slides toward a tip end of the barrel, and bends about the bottom of the annular groove in such a manner that the bendable portion falls in a direction radially inwardly with respect to the gasket when the gasket is held in intimate contact with a inner wall surface of the barrel and slides toward a back end of the barrel, wherein the curved surface of said bendable portion includes a portion which is held in intimate contact with the inner wall surface of the barrel when the gasket is bent, the portion of the curved surface which is held with the inner wall surface of the barrel when the gasket is bent being formed with a radius $R_2$, and wherein a distance $R_1$ between the bottom of said annular groove and a crest of said curved surface is smaller than the radius $R_2$.

2. An injector according to claim 1, wherein said gasket is made of a synthetic resin having an A-scale Shore hardness in the range from 20 to 70.

3. An injector according to claim 2, wherein said synthetic resin comprises one selected from the group consisting of a polystyrene elastomer, a polyolefin elastomer, a polyester elastomer, a polyamide elastomer, a polyvinyl chloride elastomer, and styrene-butadiene rubber with polystyrene added.

* * * * *